United States Patent
Kim et al.

(10) Patent No.: US 10,954,405 B2
(45) Date of Patent: Mar. 23, 2021

(54) WATER-BASED DIACETYLENE INK, HYDROCHROMIC POLYDIACETYLENE PAPER PREPARED USING THE INK, AND USE THEREOF

(71) Applicant: INDUSTRY-UNIVERSITY COOPERATION FOUNDATION HANYANG UNIVERSITY, Seoul (KR)

(72) Inventors: Jong-Man Kim, Seoul (KR); Dong-Hoon Park, Ansan-si (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 354 days.

(21) Appl. No.: 15/772,200

(22) PCT Filed: Oct. 12, 2016

(86) PCT No.: PCT/KR2016/011398
§ 371 (c)(1),
(2) Date: Apr. 30, 2018

(87) PCT Pub. No.: WO2017/073926
PCT Pub. Date: May 4, 2017

(65) Prior Publication Data
US 2018/0312708 A1 Nov. 1, 2018

(30) Foreign Application Priority Data

Oct. 30, 2015 (KR) .................. 10-2015-0151931
Sep. 27, 2016 (KR) .................. 10-2016-0123841

(51) Int. Cl.
| | | |
|---|---|---|
| *C09D 11/50* | (2014.01) | |
| *B41M 3/00* | (2006.01) | |
| *B41M 7/00* | (2006.01) | |
| *C07D 233/61* | (2006.01) | |
| *C09D 11/033* | (2014.01) | |
| *C09D 11/102* | (2014.01) | |
| *C09D 11/328* | (2014.01) | |
| *C09D 11/38* | (2014.01) | |
| *C09D 11/106* | (2014.01) | |
| *G06K 9/00* | (2006.01) | |

(52) U.S. Cl.
CPC .............. *C09D 11/50* (2013.01); *B41M 3/00* (2013.01); *B41M 3/006* (2013.01); *B41M 7/0081* (2013.01); *C07D 233/61* (2013.01); *C09D 11/033* (2013.01); *C09D 11/102* (2013.01); *C09D 11/106* (2013.01); *C09D 11/328* (2013.01); *C09D 11/38* (2013.01); *G06K 9/00* (2013.01)

(58) Field of Classification Search
CPC ..... C09D 11/50; C09D 11/033; C09D 11/102; C09D 11/328; C09D 11/38; C09D 11/106; C07D 233/61; B41M 3/006; B41M 7/0081; B41M 3/00; G06K 9/00
See application file for complete search history.

(56) References Cited

PUBLICATIONS

Park et al., "Inkjet-Printable Amphiphilic Polydiacetylene Precursor for Hydrochromic Imaging on Paper", Adv. Funct. Mater., Published online Dec. 15, 2015, vol. 26, pp. 498-506.*

* cited by examiner

*Primary Examiner* — Patrick D Niland
(74) *Attorney, Agent, or Firm* — Sughrue Mion, PLLC

(57) ABSTRACT

A water-based ink comprising a diacetylene monomer, a hydrochromic polydiacetylene paper prepared using the ink, and uses therefor are provided. The water-based ink includes a diacetylene monomer, and a solvent mixture comprising water and an alcohol. The diacetylene monomer has a ionic functional group represented by $R^+X^-$, wherein $X^-$ is $F^-$, $Cl^-$, $Br^-$, $I^-$, $PF_6^-$, $BF_4^-$, bis(trifluoromethane)sulfonimide (TFSI) ($Tf_2N^-$), trifluoromethanesulfonate ($TfO^-$), $SCN^-$, or $CH_3COO^-$, and $R^+$ is $N^+$—$R_1$-heterocyclic quaternary ammonium.

16 Claims, 8 Drawing Sheets

【FIG. 1】
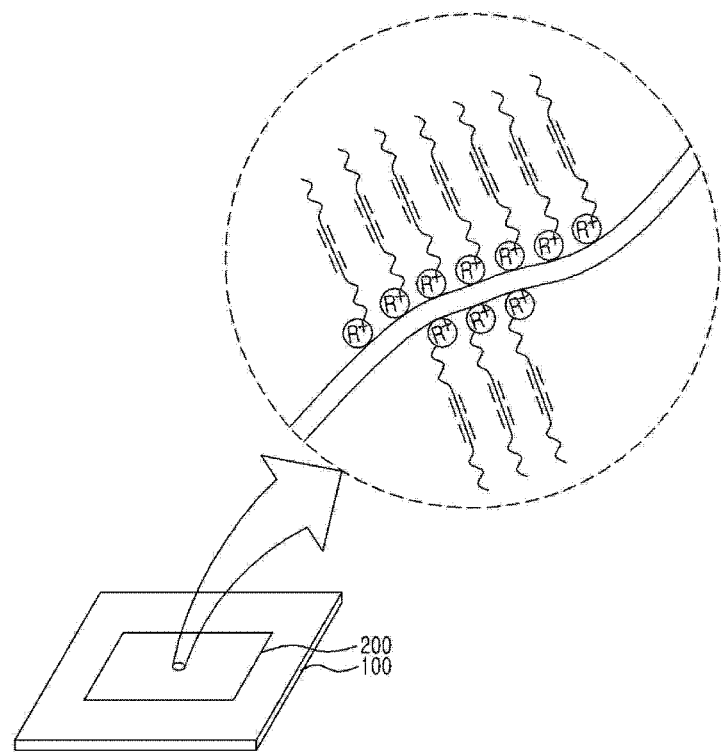
【FIG. 2】
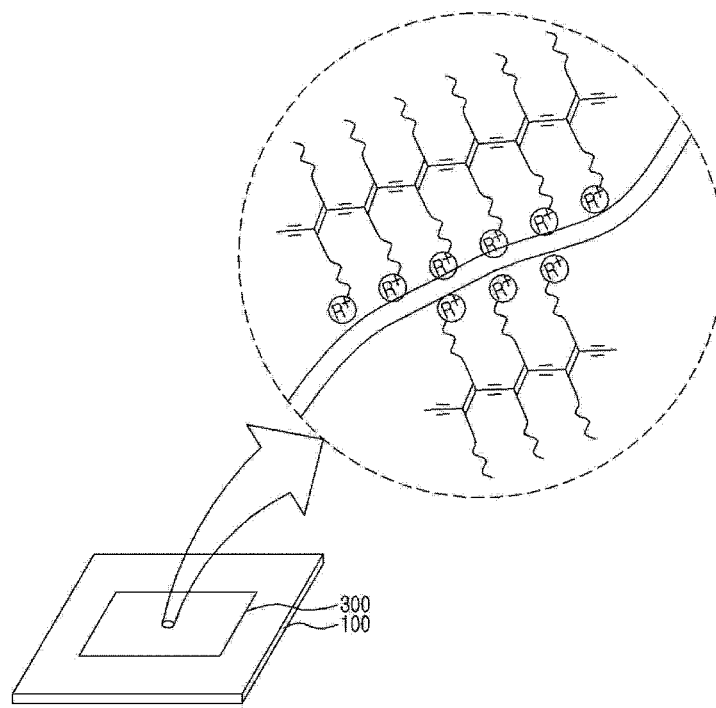

【FIG. 3】
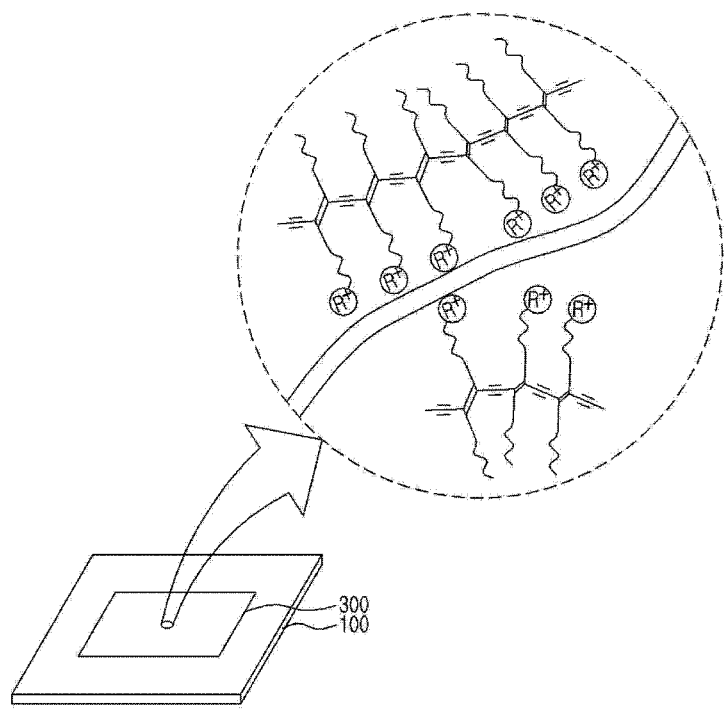
【FIG. 4】
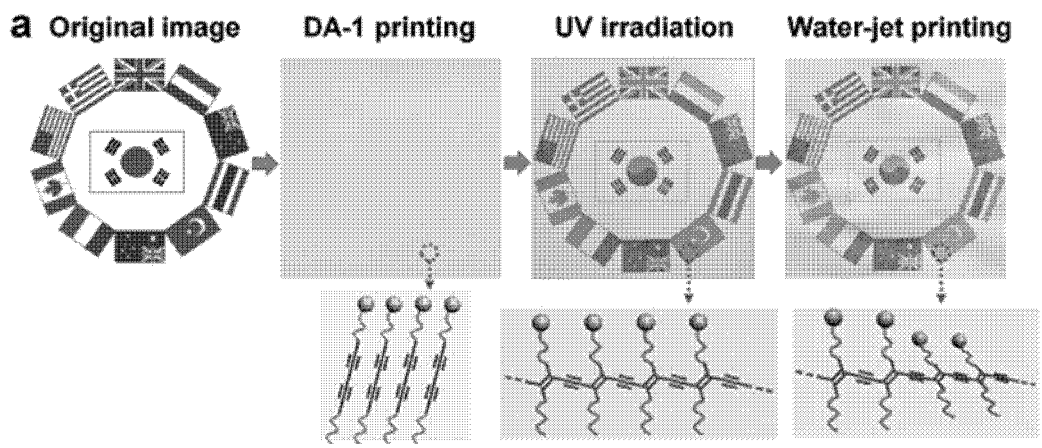

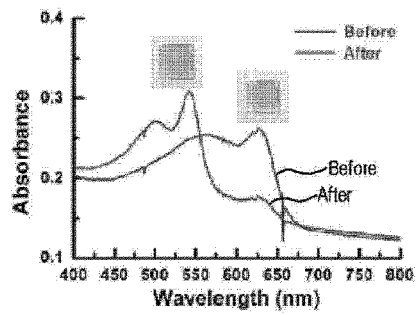
[FIG. 5A]
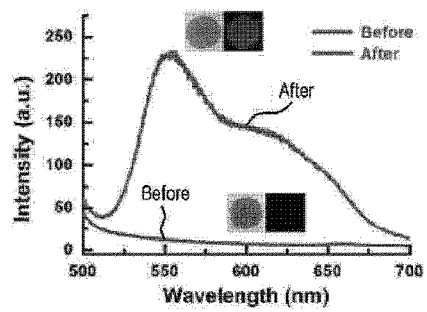
[FIG. 5B]
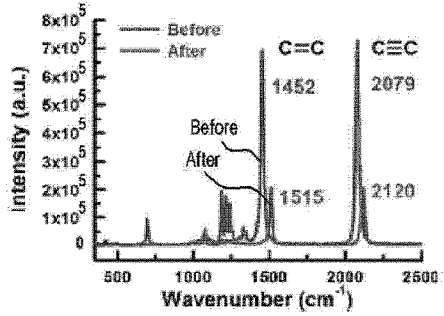
[FIG. 5C]
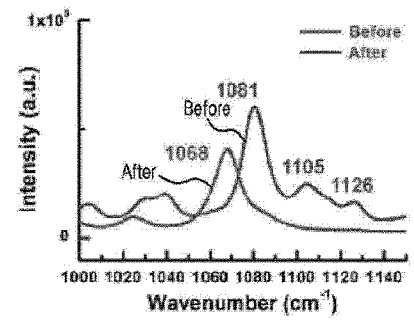
[FIG. 5D]
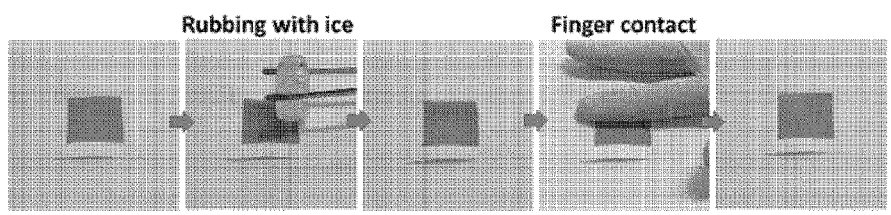
[FIG. 6A]
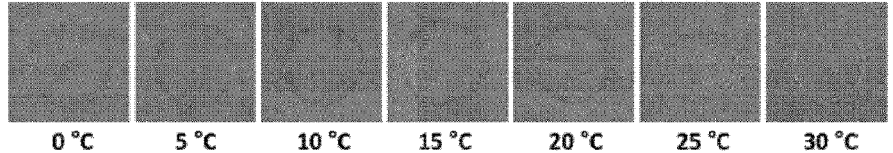
[FIG. 6B]
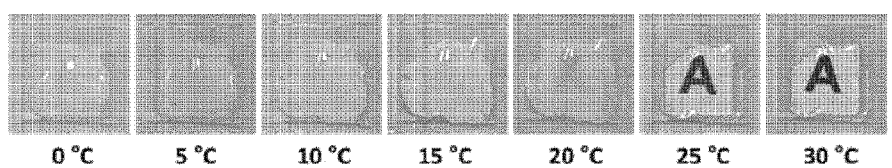
[FIG. 6C]

【FIG. 7】
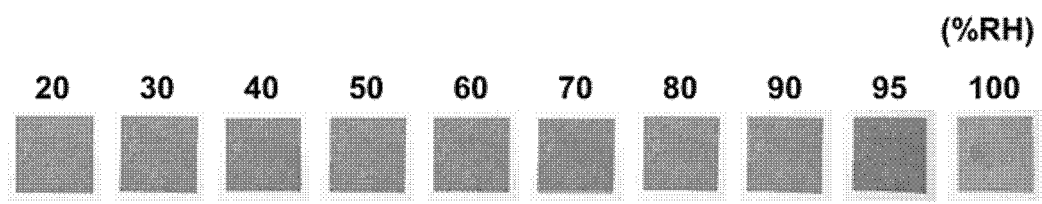
【FIG. 8】
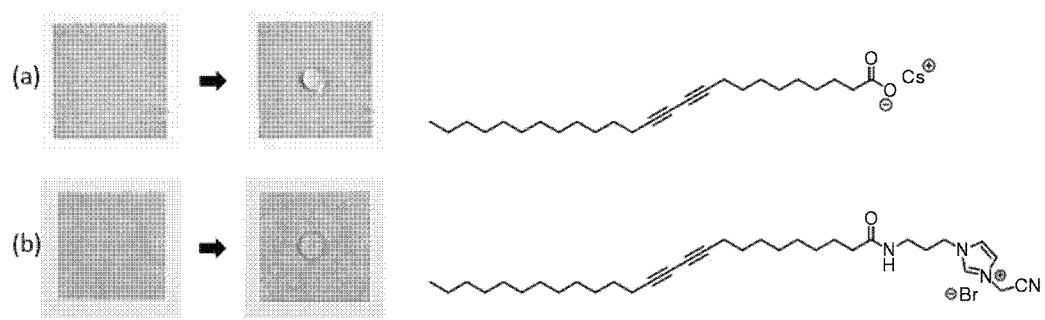
【FIG. 9】
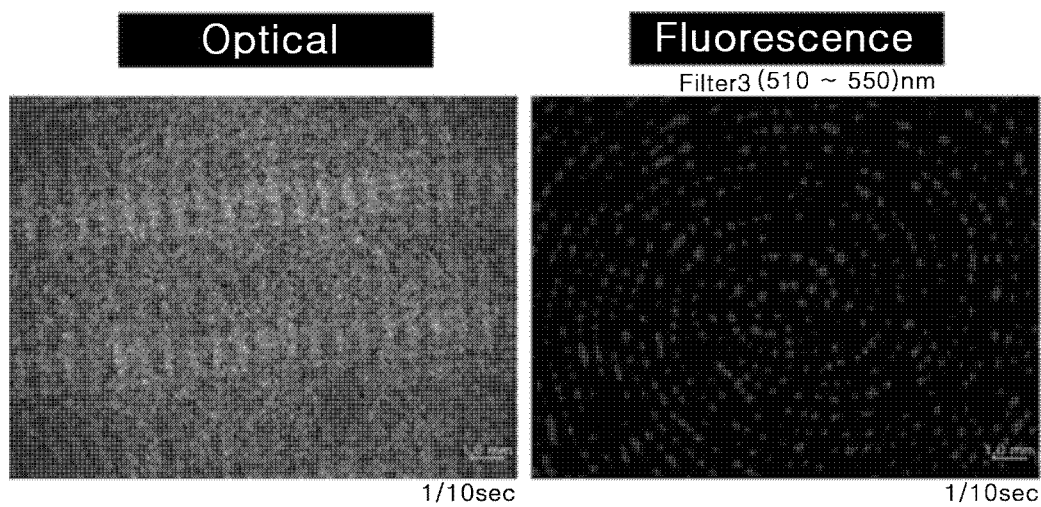

[FIG. 10]
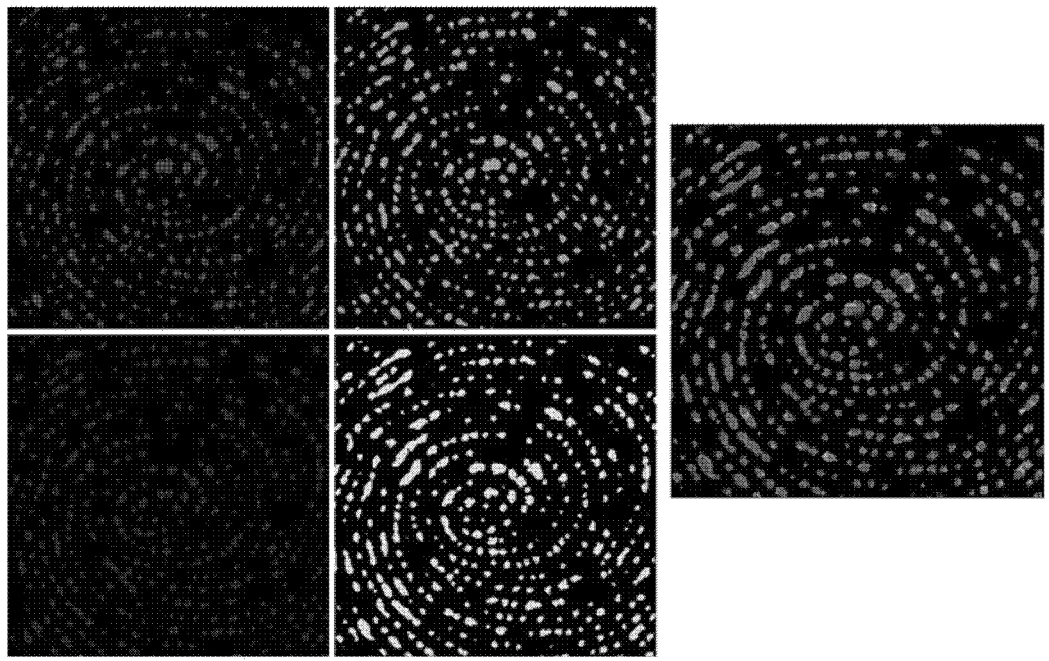
[FIG. 11]
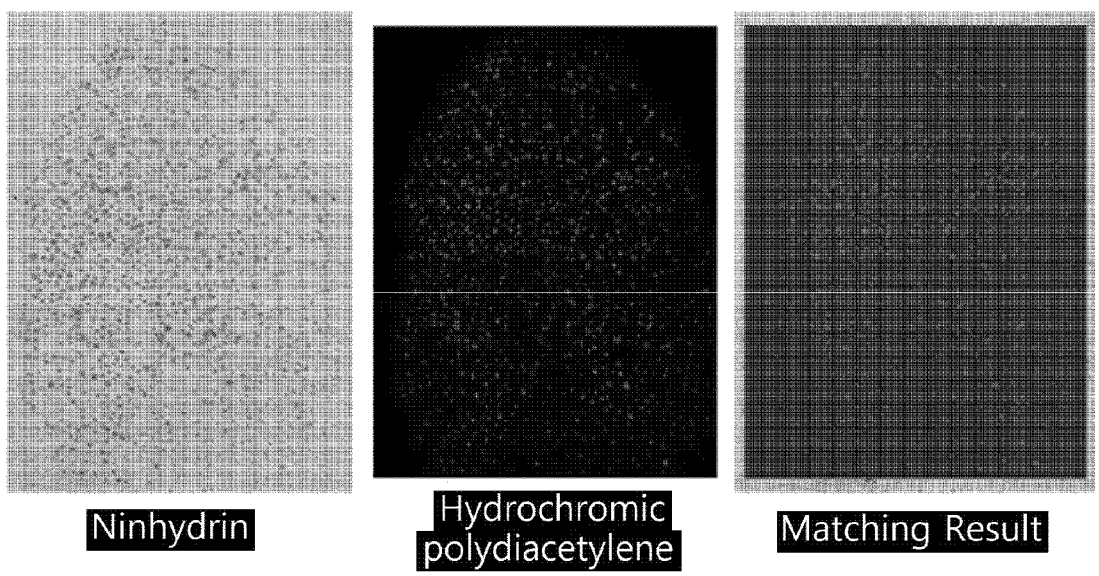

[FIG. 12]
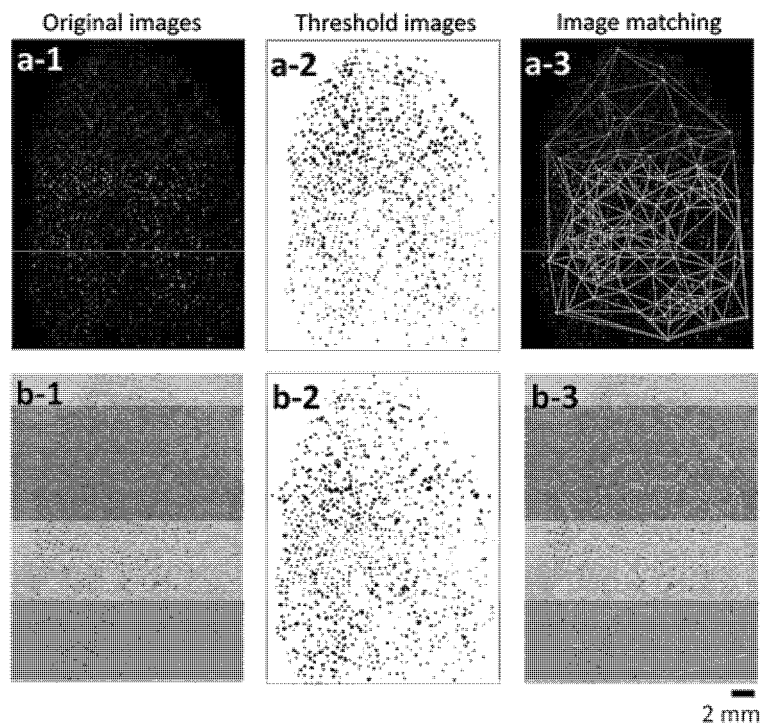
[FIG. 13]
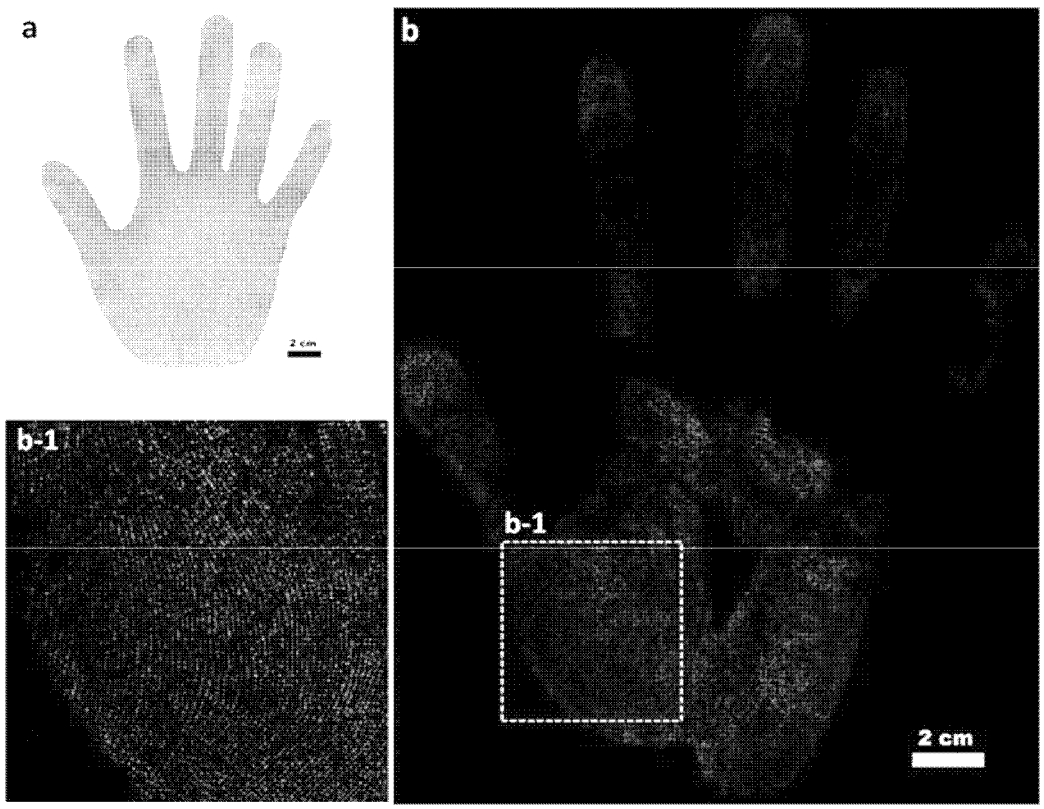

[FIG. 14]
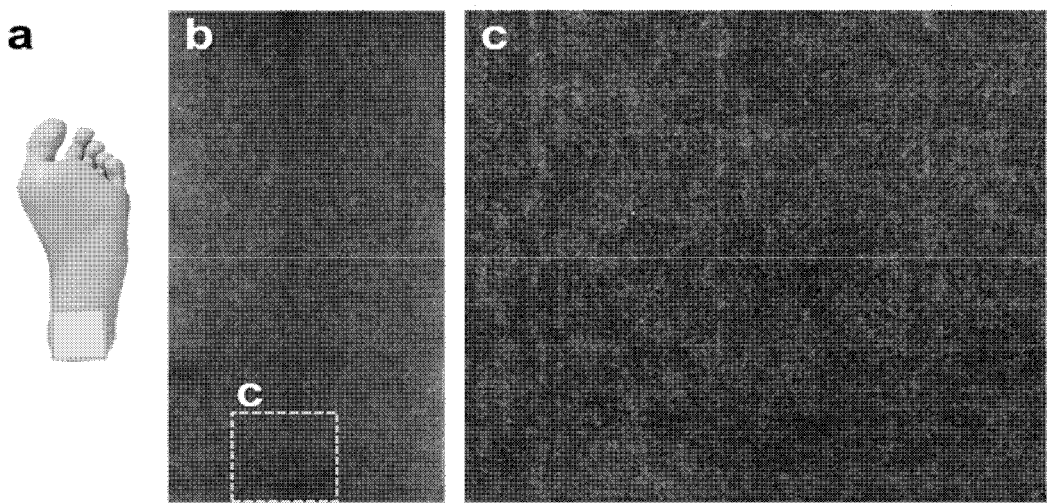
[FIG. 15]
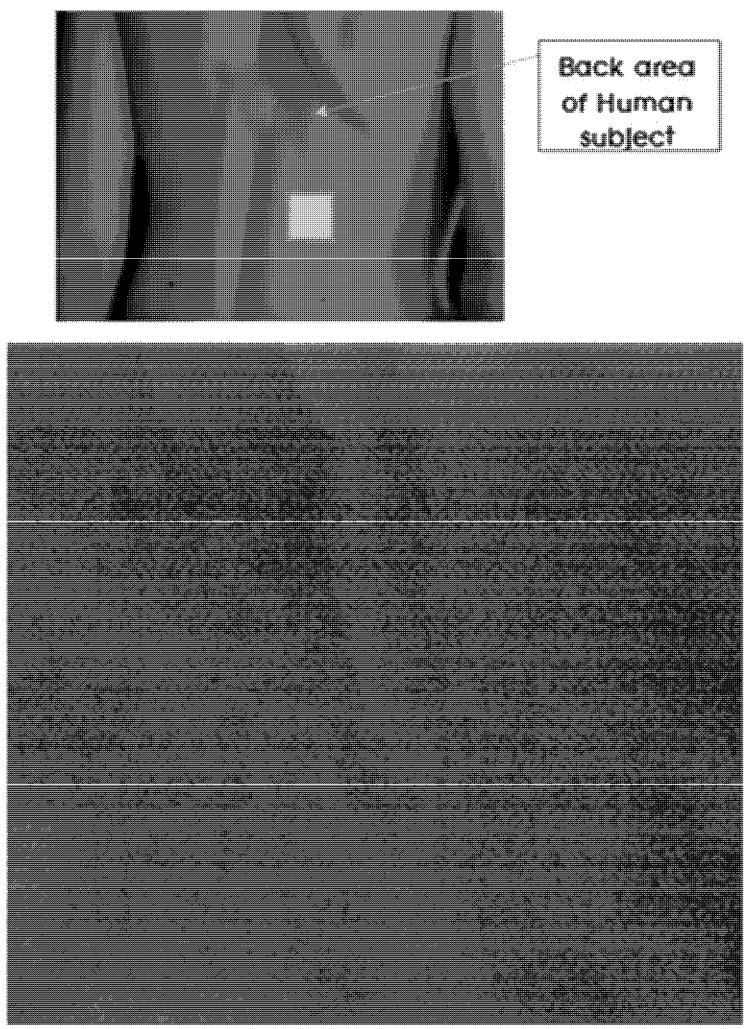

[FIG. 16]
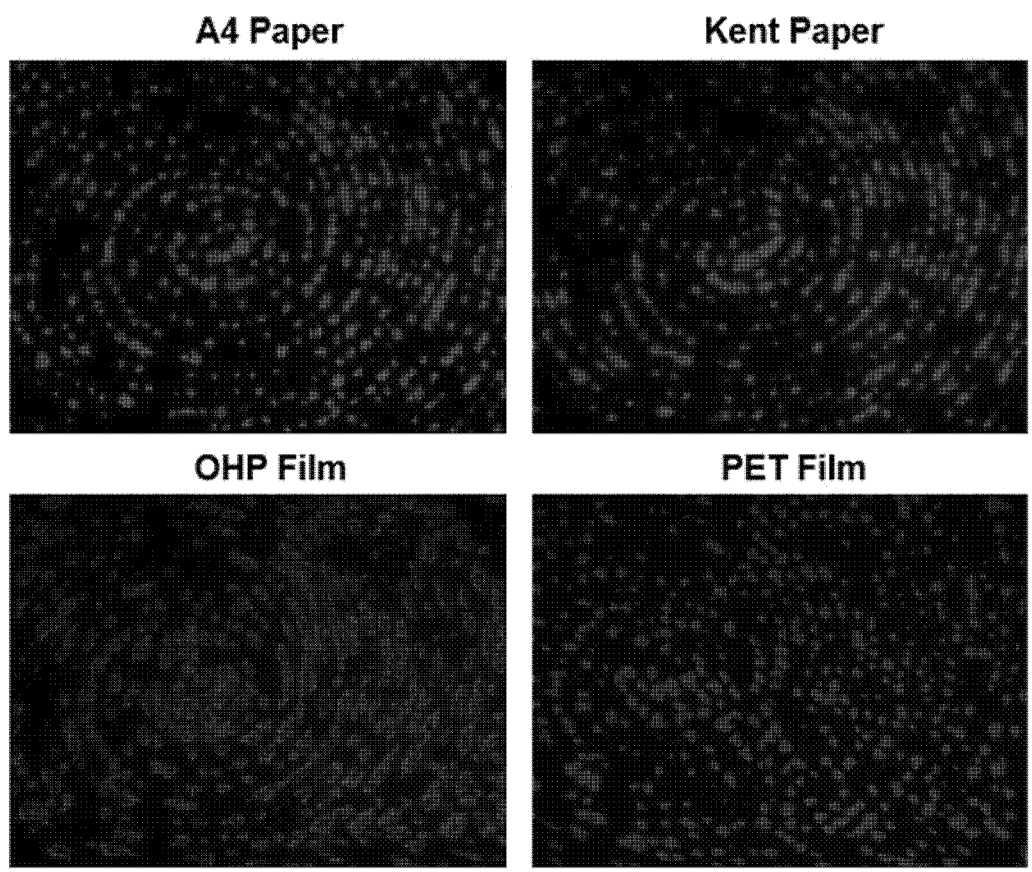

WATER-BASED DIACETYLENE INK, HYDROCHROMIC POLYDIACETYLENE PAPER PREPARED USING THE INK, AND USE THEREOF

CROSS REFERENCE TO RELATED APPLICATIONS

This application is a National Stage of International Application No. PCT/KR2016/011398 filed Oct. 12, 2016, claiming priority based on Korean Patent Application No. 10-2015-0151931 filed Oct. 30, 2015 and Korean Patent Application No. 10-2016-0123841 filed Sep. 27, 2016.

TECHNICAL FIELD

The present invention relates to polydiacetylene, and more particularly, to a hydrochromic polydiacetylene moisture test paper.

BACKGROUND ART

Polydiacetylene, which is a polymer of diacetylene monomers, is a conjugated polymer prepared by photopolymerization such as irradiation with ultraviolet rays or gamma rays when diacetylene monomers are arranged through self-assembly. Such a polydiacetylene polymer has double bonds and triple bonds alternatively present in a main chain thereof and generally exhibits a blue color while having a maximum absorption wavelength at about 640 nm. The maximum absorption wavelength of polydiacetylene shifts to about 540 nm and the color thereof is changed to red by changes in the external environment (heat, solvent, pH, force, molecular recognition, etc.). Various sensors are being researched and developed using such color change characteristics of polydiacetylene.

Conventional technologies are disadvantageous in that a prepared film is detached or easily peeled off when glass, a PET film, or an OHP film is used as a base material for preparing a hydrochromic polydiacetylene thin film. In addition, upon fabrication of a large-area thin film, a large amount of hydrochromic polydiacetylene complex is necessary and the generated thin film may be non-uniform. Further, during storage after fabrication of a thin film, the fabricated thin film sensitively reacts with moisture in the atmosphere, whereby a sensor function thereof may be lost.

DISCLOSURE

Technical Problem

Therefore, the present invention has been made in view of the above problems, and it is one object of the present invention to provide a polydiacetylene-containing moisture test paper having an excellent binding force to a base material and exhibiting reduced sensitivity to humidity.

It will be understood that technical problems of the present invention are not limited to the aforementioned problems and other technical problems not referred to herein will be clearly understood by those skilled in the art from the description below.

Technical Solution

According to an embodiment of the present invention, a water-based ink comprising a diacetylene monomer is provided. The water-based ink includes a diacetylene monomer represented by Formula 1 below, and a solvent mixture comprising water and an alcohol:

[Formula 1]

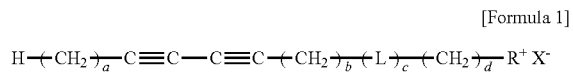

wherein a is an integer of 1 to 20, b is an integer of 1 to 20, c is an integer of 0 to 2, d is an integer of 1 to 10, L is

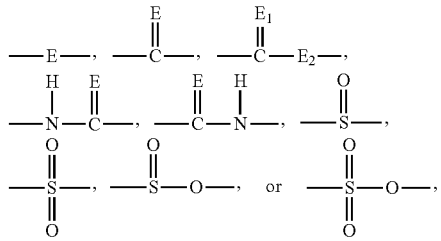

E, $E_1$, and $E_2$ are each independently O or S, $X^-$ is $F^-$, $Cl^-$, $Br^-$, $I^-$, $PF_6^-$, $BF_4^-$, bis(trifluoromethane)sulfonimide (TFSI) ($Tf_2N^-$), trifluoromethanesulfonate ($TfO^-$), $SCN^-$, or $CH_3COO^-$, $R^+$ is $N^+$—$R_1$-heterocyclic quaternary ammonium represented by Formula 2a below, and $R^+$ and $X^-$ forms $N^+$—$R_1$-heterocyclic quaternary ammonium salt:

[Formula 2a]

wherein ring B is a 5-membered or 6-membered heterocyclic compound which is saturated or unsaturated and has 1 to 3 atoms of N and 0 to 1 atoms of O as heteromembers, $R_1$ is a C1 to C16 cyanoalkyl, a C1 to C16 haloalkyl, a C1 to C16 hydroxyalkyl, or a C1 to C16 aminoalkyl, and * represents a bond.

The $N^+$—$R_1$-heterocyclic quaternary ammonium represented by Formula 2a may be $N^+$—$R_1$-heterocyclic quaternary ammonium represented by Formula 2b or 2c below:

[Formula 2b]

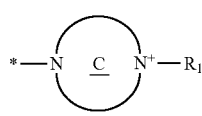

[Formula 2c]

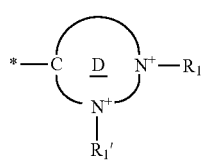

wherein, in Formula 2b, ring C may be a 5-membered or 6-membered unsaturated heterocyclic compound comprising 2 to 3 atoms of N as heteromembers, in Formula 2c, ring D may be a 5-membered or 6-membered unsaturated heterocyclic compound comprising 2 to 3 atoms of N as heteromembers, and $R_1$ and $R_1'$ may be each independently a C1 to C16 cyanoalkyl, a C1 to C16 haloalkyl, a C1 to C16 hydroxyalkyl, or a C1 to C16 aminoalkyl.

The $N^+$—$R_1$-heterocyclic quaternary ammonium may be $N^+$—$R_1$-azolium, $N^+$—$R_1$-azinium, or $N^+$—$R_1R_2$-piperazinium.

The $N^+$—$R_1$-azolium may be $N^+$—$R_1$-diazolium or $N^+$—$R_1$-triazolium. The $N^+$—$R_1$-diazolium may be $N^+$—$R_1$-imidazolium represented by Formula 2-1 below or $N^+$—$R_1$-pyrazolium represented by Formula 2-2 below. The $N^+$—$R_1$-triazolium may be represented by Formula 2-3 below.

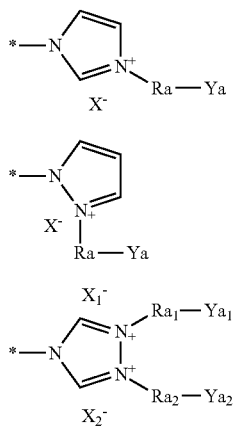

In Formula 2-1 or 2-2, $R_a$ may be a C1 to C16 alkylene group, and $Y_a$ may be a cyano group, a halogen, a hydroxyl group, or an amine group. In Formula 2-3, wherein $R_{a1}$ and $R_{a2}$ may be each independently a C1 to C16 alkylene group, and $Y_{a1}$ and $Y_{a2}$ may be each independently a cyano group, a halogen, a hydroxyl group, or an amine group.

The alcohol may be an ethyl alcohol. A volumetric ratio of the water to the alcohol may be 1:0.03 to 1:0.7. The diacetylene monomer may be contained at a concentration of 50 to 300 mM.

According to another embodiment of the present invention, a moisture test paper is provided. The moisture test paper comprises a paper substrate comprising cellulose fibers which are irregularly entangled. A polydiacetylene region comprising hydrochromic polydiacetylene represented by Formula 3 below is disposed on the paper substrate:

[Formula 3]

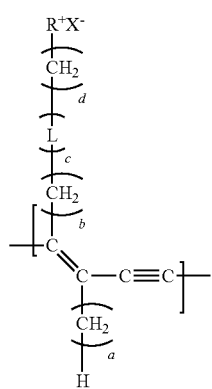

a, b, c, d, L, $R^+$, and $X^-$ in Formula 3 may be respectively the same as a, b, c, d, L, $R^+$, and $X^-$ in Formula 1.

The polydiacetylene region may be blue. The polydiacetylene region may change color by water at about 20° C. or more. —OH groups of the cellulose fibers of the paper substrate may be exposed. The moisture test paper may be a paper for mapping sweat pores.

According to still another embodiment of the present invention, a method of manufacturing a moisture test paper is provided. The method comprises a step of printing the water-based ink containing diacetylene monomers represented by Formula 1 on a paper substrate comprising cellulose fibers which are irregularly entangled. The ink printed on the paper substrate is dried to form a diacetylene region in which the diacetylene monomers are self-assembled and disposed. The diacetylene region is irradiated with ultraviolet rays or gamma rays to photopolymerize the diacetylene monomers and, accordingly, form hydrochromic polydiacetylene.

—OH groups of the cellulose fibers of the paper substrate may be exposed. The moisture test paper may be a paper for mapping sweat pores.

Advantageous Effects

As described above, a diacetylene monomer according to the present invention includes quaternary ammonium cations and, accordingly, a water-based ink can be obtained by dissolving the diacetylene monomer in a solvent mixture including water and ethanol. In addition, quaternary ammonium in the diacetylene monomer interacts with cellulose fibers of a paper substrate, thereby having an excellent binding force to the paper substrate. Accordingly, the diacetylene monomer or polydiacetylene formed by photopolymerizing the diacetylene monomer can be prevented from being separated from the paper substrate. Further, polydiacetylene can have reduced sensitivity to humidity.

However, it will be understood that effects of the present invention are not limited to those mentioned above and other unmentioned technical effects will be clearly understood by those skilled in the art from the description below.

DESCRIPTION OF DRAWINGS

Example embodiments of the present invention will become more apparent by describing in detail example embodiments of the present invention with reference to the accompanying drawings, in which:

FIG. 1 illustrates a schematic diagram of a moisture test paper according to an embodiment of the present invention;

FIG. 2 illustrates a schematic diagram of a moisture test paper according to another embodiment of the present invention;

FIG. 3 is a schematic diagram illustrating color change of the moisture test paper illustrated in FIG. 2;

FIG. 4 is a set of schematic diagrams illustrating a moisture test paper manufactured according to the moisture test paper manufacture example and results obtained by applying moisture to a selected region of the moisture test paper;

FIGS. 5A-5D illustrate graphs of a) UV-vis absorption spectrum, b) fluorescence emission spectrum, and c, d) Raman spectrum before and after applying moisture to the moisture test paper manufactured according to the moisture test paper manufacture example;

FIGS. 6A-6C are a set of photographs illustrating the temperature-dependent reaction of the moisture test paper manufactured according to the moisture test paper manufacture example and solubility of DA-1 in water dependent upon temperature;

FIG. 7 is a photograph illustrating a relative humidity-dependent hydrochromic degree of the moisture test paper manufactured according to the moisture test paper manufacture example;

FIG. 8 is a set of photographs illustrating hydrochromic characteristics of the moisture test papers according to the moisture test paper manufacture example (b) and the moisture test paper comparison example (a);

FIG. 9 illustrates an optical image and a fluorescence image after a thumb touches the moisture test paper manufactured according to the moisture test paper manufacture example;

FIG. 10 illustrates fluorescence images obtained after respectively contacting a thumb on four different moisture test papers manufactured according to the moisture test paper manufacture example;

FIG. 11 illustrates comparison photographs of a fluorescence image obtained after a thumb contacts the moisture test paper manufactured according to the moisture test paper manufacture example and a potential fingerprint obtained using the same thumb and ninhydrin;

FIG. 12 illustrates a threshold image (a-2) in which only sweat pores are exposed, using a position tracking method, from a sweat pore distribution (a-1) obtained using the moisture test paper manufactured according to the moisture test paper manufacture example, a sweat pore distribution (b-1) for the same finger obtained using ninhydrin, and a threshold (b-2) image in which only sweat pores are exposed, using position tracking, from the sweat pore distribution (b-1);

FIG. 13 illustrates sweat pore distribution test results on the entire palm of a hand using a moisture test paper;

FIG. 14 illustrates test results of the distribution of sweat pores in the sole using a moisture test paper;

FIG. 15 illustrates test results of the distribution of sweat pores in the back using a moisture test paper; and FIG. 16 is a set of photographs illustrating thumb sweat pore distribution test results of an A4 paper, a Kent paper, an OHP film, and a PET film, which have been printed with the ink prepared according to the ink preparation example.

MODES OF THE INVENTION

Hereinafter, the present invention will be described in detail by describing exemplary embodiments of the invention with reference to the attached drawings. However, the scope of the present invention is not limited to the embodiments described in the present specification and may be embodied in other forms. In the drawings, it will be understood that when a layer is referred to as being "on" another layer or substrate, it can be directly formed on the other layer or substrate or a third layer can be interposed therebetween. In embodiments herein, it will be understood that "first", "second", or "third" are not provided to limit components and are only provided to distinguish components from one another.

In the present specification, "alkyl" may refer to an aliphatic hydrocarbon group or a "saturated alkyl" having no double bonds or triple bonds, unless specified otherwise. The saturated alkyl group may be a linear alkyl group.

In the present specification, unless specified otherwise, "alkylene" may refer to a divalent radical of an alkane, which is a saturated hydrocarbon, and may be a linear alkylene.

In the present specification, when the expression "Cx to Cy" is used, it should be understood that all integer carbon numbers between x and y are should be interpreted as described. In the present specification, "halogen" or "halo" is an element belonging to Group 17 and, particularly, may be fluorine, chlorine, bromine, or iodine.

In the present specification, when the expression "x to y" is used, it should be understood that all numbers between x and y are should be interpreted as described.

Diacetylene Monomer

An embodiment of the present invention provides a diacetylene monomer represented by Formula 1 below:

[Formula 1]

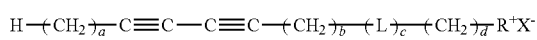

wherein a is an integer of 1 to 20. For example, a may be an integer of 6 to 18, particularly an integer of 10 to 12. b may be an integer of 1 to 20. For example, b may be an integer of 2 to 12, particularly an integer of 2 to 8.

In Formula 1, L may be

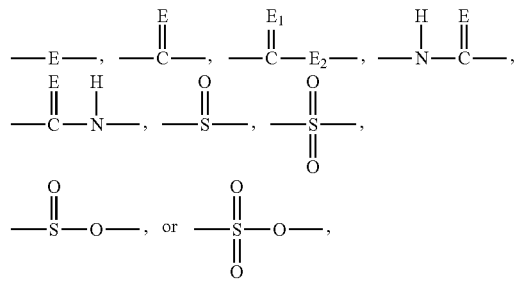

and E, $E_1$, and $E_2$ may be each independently O or S. c may be an integer of 0 to 2. For example, c may be 1. d may be an integer of 1 to 10. For example, d may be an integer of 1 to 5, particularly an integer of 2 to 4.

In addition, $R^+$ may be a quaternary ammonium group. For example, the quaternary ammonium may be $N^+$—$R_1$-heterocyclic quaternary ammonium represented by Formula 2a below:

[Formula 2a]

wherein ring B may be a 5-membered or 6-membered heterocyclic compound, may be a saturated or unsaturated heterocyclic compound, and may include at least one atom of N. Particularly, ring B may include 1 to 3 atoms of N and 0 to 1 atoms of O as heteromembers. In addition, in Formula 2a, $R_1$ may be a C1 to C16 cyanoalkyl, a C1 to C16 haloalkyl, a C1 to C16 hydroxyalkyl, or a C1 to C16 aminoalkyl. Particularly, $R_1$ may be represented by *—$R_a$—$Y_a$. Here, * may represent a bond, and $R_a$ may be a C1 to C16 alkylene group. For example, $R_a$ may be a C1 to C6 alkylene group, particularly a C1 to C3 alkylene group. $Y_a$ may be a cyano group, a halogen, a hydroxyl group, or an amine group.

The $N^+$—$R_1$-heterocyclic quaternary ammonium represented by Formula 2a may be $N^+$—$R_1$-heterocyclic quaternary ammonium represented by Formula 2b or 2c below:

[Formula 2b]

[Formula 2c]

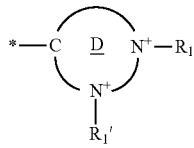

Formula 2b may be *—N⁺—R₁-heterocyclic quaternary ammonium. Here, ring C may be a 5-membered or 6-membered unsaturated heterocyclic compound and may include 2 to 3 atoms of N as heteromembers.

In Formula 2c, ring D may be a 5-membered or 6-membered unsaturated heterocyclic compound and may include 2 to 3 atoms of N as heteromembers. In addition, $R_1$ and $R_1'$ may be each independently a C1 to C16 cyanoalkyl, a C1 to C16 haloalkyl, a C1 to C16 hydroxyalkyl, or a C1 to C16 aminoalkyl, and may be represented by *—$R_a$—$Y_a$. $R_a$ and $Y_a$ may be defined as above.

The N⁺—R₁-heterocyclic quaternary ammonium may be, for example, N⁺—R₁-azolium, N⁺—R₁-azinium, or N⁺—R₁R₂-piperazinium.

The N⁺—R₁-azolium may be N⁺—R₁-diazolium or N⁺—R₁-triazolium. The N⁺—R₁-diazolium may be N⁺—R₁-imidazolium or N⁺—R₁-pyrazolium, the N⁺—R₁-imidazolium may be represented by Formula 2-1 below, and the N⁺—R₁-pyrazolium may be represented by Formula 2-2 below. Meanwhile, N⁺—R₁-triazolium may be represented by Formula 2-3 below:

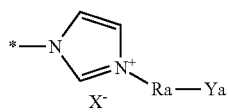
(2-1)

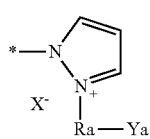
(2-2)

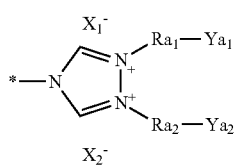
(2-3)

The N⁺—R₁-azinium may be N⁺—R₁-pyridiminium or N⁺—R₁-pyrazinium. The N⁺—R₁-pyridiminium may be represented by Formula 2-7 or 2-8 below, and N⁺—R₁-pyrazinium may be represented by Formula 2-9 below:

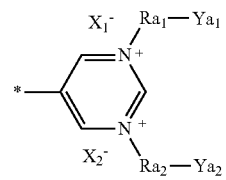
(2-7)

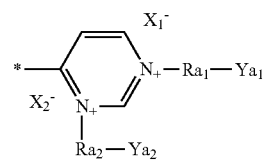
(2-8)

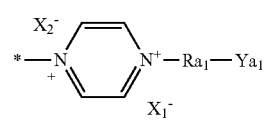
(2-9)

The N⁺—R₁R₂-piperazinium may be *—N⁺—R₁R₂-piperazinium and may be represented by Formula 2-14 below:

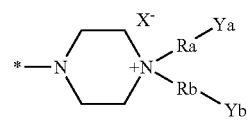
(2-14)

In Formulas 2-1 to 2-3, 2-7 to 2-9, and 2-14, $R_a$ and $Y_a$ may be the same as described above, $R_{a1}$ and $R_{a2}$ may be each independently a C1 to C16 alkylene group, for example, a C1 to C6 alkylene group, particularly a C1 to C3 alkylene group, and $Y_{a1}$ and $Y_{a2}$ may be each independently a cyano group, a halogen, a hydroxyl group, or an amine group. $R_b$ may be a C1 to C16 alkylene group. $R_b$ may be, for example, a C1 to C6 alkylene group, particularly a C1 to C3 alkylene group. $Y_b$ may be hydrogen, a cyano group, a halogen, a hydroxyl group, or an amine group.

The diacetylene monomer may further include counter anions. The counter anions (X⁻, $X_1^-$, $X_2^-$) may be F⁻, Cl⁻, Br⁻, I⁻, $PF_6^-$, $BF_4^-$, bis(trifluoromethane)sulfonimide ($Tf_2N^-$), trifluoromethanesulfonate (TfO⁻), SCN⁻, or $CH_3COO^-$.

As such, the diacetylene monomer contains a quaternary ammonium group at one end of an aliphatic hydrocarbon chain thereof, thereby exhibiting amphiphilic properties. The quaternary ammonium group increases the water solubility of the diacetylene monomer exhibiting amphiphilic properties, thereby allowing easy dissolution in a polar protic solvent, particularly water. In other words, the diacetylene monomer may exhibit overall water solubility. Further, when $R_1$ bonded to N⁺ of the quaternary ammonium group is *—$R_a$—$Y_a$, i.e., a cyanoalkyl, a haloalkyl, a hydroxyalkyl, or an aminoalkyl, solubility may be further increased.

Water-Based Ink for Paper Printing Including Diacetylene Monomer

The water-based ink according to an embodiment of the present invention may include the aforementioned diacetylene monomer and a solvent. The solvent may be a polar protic solvent. The polar protic solvent may be water, an alcohol, or a combination thereof. For example, the solvent may be a mixture of water and an alcohol. The alcohol may be a monohydric alcohol or a polyhydric alcohol having two or more OH groups. For example, the alcohol may be methyl alcohol, ethyl alcohol, or ethylene glycol.

A volumetric ratio of the water to the alcohol may be 1:0.03 to 1:0.7. The volumetric ratio may be, for example, 1:0.1 to 1:0.5, more particularly 1:0.2 to 1:0.3. In addition, the diacetylene monomer may be contained at a concentration of 50 to 300 mM.

As described above, the diacetylene monomer includes quaternary ammonium cations, thereby being dissolved in the polar protic solvent. Accordingly, the ink may be a homogeneous solution wherein the diacetylene monomer is dissolved in the solvent. Particularly, the diacetylene monomers in the ink might not have a self-assembled form like micelles. In addition, the ink may be transparent and colorless.

In particular, gelation may occur when the diacetylene monomer is mixed with water. Accordingly, an alcohol is added to prevent gelation, thereby obtaining the homogeneous solution. In other words, an alcohol further increases the solubility of the diacetylene monomer, thereby lowering the viscosity of the ink.

Such a homogeneous ink solution may greatly reduce clogging of an ink cartridge when it is put into an ink cartridge and printing is performed.

In addition, the ink may exclude a surfactant. Further, the ink may include only the diacetylene monomer and a solvent.

Test Paper on which Ink Containing Diacetylene Monomer is Printed

FIG. 1 illustrates a schematic diagram of a moisture test paper according to an embodiment of the present invention.

Referring to FIG. 1, a paper substrate 100 may be provided. As the paper substrate 100 includes irregularly entangled cellulose fibers, among various types of paper substrates, the paper substrate 100 may be an uncoated paper, a surface of which is not coated with a paint or the like. Further, the paper substrate 100 may be a printing paper used in printers and, particularly, may be an uncoated printing paper, but the present invention is not limited thereto. The paper substrate 100 may be any one so long as a surface thereof is hydrophilic, particularly a —OH functional group is exposed on a surface thereof.

A diacetylene region in which the diacetylene monomer is disposed, i.e., the DA region 200, may be disposed on the paper substrate 100. The DA region 200 may be a region on which the aforementioned ink containing the diacetylene monomer is applied, particularly a region in which a solvent is dried after application of the ink. Here, to perform the application, the ink is injected into a cartridge, and then an inkjet printer is used. Meanwhile, it is obvious that the shape of the DA region 200 is not limited to those illustrated in the accompanying drawings and may be printed in a shape desired by a user.

The diacetylene monomer may be present in a self-assembled state in the DA region 200. In particular, quaternary ammonium cation groups ($R^+$) are disposed adjacently onto cellulose fibers on which a hydrophilic functional group, particularly an OH group, is exposed, and aliphatic hydrocarbon chains including diacetylene groups may be self-assembled on the cellulose fibers while being disposed outward. However, the present invention is not limited to this theory. The diacetylene monomer may be partially coagulated and self-assembled while being physically adsorbed onto the cellulose fibers.

The DA region 200 may be a colorless transparent area. However, the DA region 200 may be converted to blue by ultraviolet irradiation described below. Accordingly, the DA layer 200 may be utilized as a pattern for distinguishing a counterfeit, and a test paper including the DA layer 200 may be utilized as a test paper having a pattern for distinguishing a counterfeit, e.g., a bill, etc.

Moisture Test Paper Having Region Containing Polydiacetylene

FIG. 2 illustrates a schematic diagram of a moisture test paper according to another embodiment of the present invention.

Referring to FIG. 2, a polydiacetylene region in which polydiacetylene is disposed, i.e., a PDA region 300, may be disposed on a paper substrate 100.

In particular, the diacetylene monomers, which have been self-assembled and thus disposed adjacent to each other, may be photopolymerized by irradiating the DA region 200 of the test paper, which has been described with reference to FIG. 1, with, particularly, ultraviolet rays of 250 to 260 nm, more particularly, ultraviolet rays of 254 nm, or gamma rays for 1 to 300 seconds, thereby forming the PDA region 300 containing polydiacetylene.

The polydiacetylene may have a repeat unit represented by Formula 3 below:

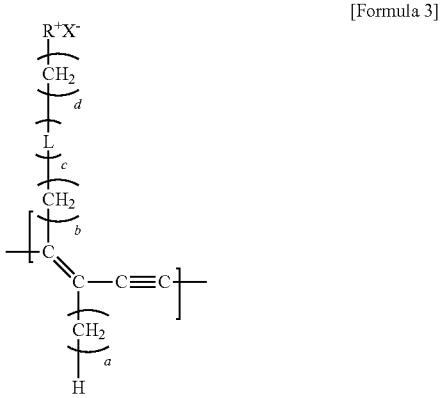

[Formula 3]

a, b, c, d, L, $R^+$, and $X^-$ in Formula 3 may be respectively the same as a, b, c, d, L, $R^+$, and $X^-$ in Formula 1.

The PDA region 300 has a maximum absorption wavelength of about 600 nm to 680 nm, particularly about 620 nm to 660 nm, for example, about 640 nm and exhibits blue, because it has highly π-conjugated main chains due to double and triple bonds of polydiacetylene alternatively arranged.

Meanwhile, hydrophilic functional groups of cellulose may have hydrophilic-hydrophilic interactions with quaternary ammonium cation groups ($R^+$) of polydiacetylene in the ink, whereby the PDA region 300 is not easily separated from the paper substrate 100. That is, a stable binding force may be exhibited.

FIG. 3 is a schematic diagram illustrating color change of the moisture test paper illustrated in FIG. 2.

Referring to FIG. 3, polydiacetylene is geometrically deformed when the PDA region 300 contacts water, whereby the maximum absorption wavelength of PDA region 300 may shift to blue to show about 490 to about 590 nm, particularly 520 to about 570 nm, for example, 540 nm while a π-conjugated main chain structure is broken. As a result, the PDA region 300 in contact with water may exhibit a red-based color. At the same time, the PDA region 300 may also generate fluorescence. Accordingly, the polydiacetylene may be referred to as a hydrochromic agent. In particular, it is presumed that diacetylene monomers, which have not formed polymers and have remained as monomers, form voids while being dissolved in water when the PDA region 300 contacts water, which causes geometric deformation of polydiacetylene. However, the present invention is not limited to this theory.

Since the color of a paper including the PDA region 300 according to an embodiment of the present invention is changed upon contact with moisture (liquid or gas) as described above, the paper may sufficiently perform a function as a moisture sensor, particularly a moisture test paper. In particular, the moisture test paper may be used to sense humidity or moisture in an organic solvent. Further, the color of the moisture test paper or the PDA may be changed from blue to red even by a very small amount of moisture, thereby being capable of being used as a paper for mapping sweat pores. In particular, the moisture test paper or the PDA serves to effectively map sweat pores of the entire body such as the palm, the soles of the feet, the back, and the face as well as the fingers, whereby the application fields thereof may be expanded. Since the moisture test paper or the PDA may be used in analyzing biometric information, such as the distribution of sweat pores in the body, as described above, it may be used in the medical field, the beauty field, or the criminal investigation field. In particular, the moisture test paper or the PDA may be used in the medical field such as analysis of the distribution of active sweat pores in patients with hyperhydrosis or analysis of sweat pore activity according to age, the cosmetic field such as development of deodorants or perspiration inhibitors, and the criminal investigation field in which sweat pore maps of fingerprints are analyzed.

Meanwhile, the color of the moisture test paper or the polydiacetylene may be changed upon contact with water at a specific temperature or more, particularly about 20° C. or more, for example, 25° C. or more. Further, the moisture test paper or the polydiacetylene may exhibit a clear color change upon contact with water at 30° C. or more. These results indicate that the moisture test paper is insensitive to moisture contained in the atmosphere, but may selectively have increased sensitivity to moisture secreted from the human body.

Hereinafter, the present invention will be described in more detail with reference to the following Examples. It should be understand that the Examples are merely provided to concretely explain the spirit of the present invention and therefore, there is no intent to limit the present invention to the Examples.

Diacetylene Monomer Synthesis Examples

Synthesis Example 1: Synthesis of DA-1 [3-(cyanomethyl)-1-(3-(pentacosa-10,12-dienamido) propyl)-1H-imidazol-3-ium bromide]

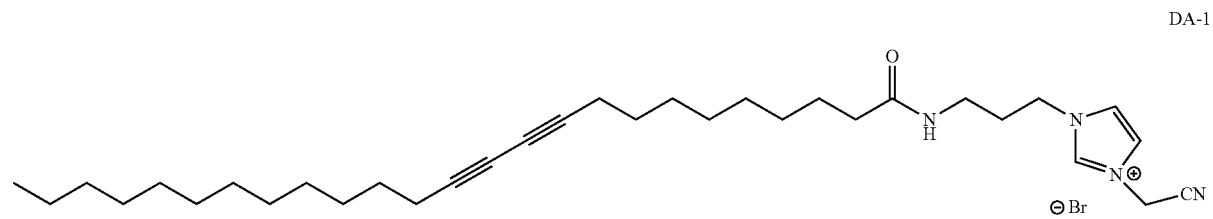 [SMILES: CCCCCCCCCCCCC#CC#CCCCCCCCCC(=O)NCCCn1cc[n+](CC#N)c1 ; [Br-]]

DA-1

A solution prepared by dissolving 10,12-pentacosadiynoic acid (PCDA, 0.75 g, 2 mmol), N-hydroxysuccinimide (NHS, 0.35 g, 3 mmol), and 1-ethyl-3-(3-dimethylaminopropyl)carbodiimide (EDC, 0.77 g, 4 mmol) in 20 ml of methylene chloride was stirred at room temperature overnight. Subsequently, the solution was concentrated in vacuo, and a residue was re-dissolved in ethyl acetate. The resultant solution was fed along with water into a separatory funnel and was allowed to be separated therein. Subsequently, a separated organic solution layer was separately isolated. The organic solution was dehydrated, and then concentrated in vacuo, thereby obtaining 2,5-dioxopyrrolidin-1-yl pentacosa-10,12-diynoate (PCDA-NHS) as a white powder. PCDA-NHS (0.94 g, 2 mmol) and triethylamine (TEA, 0.51 g, 5 mmol) were dissolved in 10 ml of methylene chloride to obtain a first solution, and 1-(3-aminopropyl) imidazole, 0.38 g, 3.00 mmol) was dissolved in 10 ml of methylene chloride to obtain a second solution. The obtained second solution was added to the first solution, followed by stirring at room temperature overnight. Subsequently, the resultant solution was concentrated in vacuo, thereby obtaining a residue. The residue was fed into a silica gel chromatography column (methylene chloride/methanol, 96/4), thereby obtaining N-(3-(1H-imidazol-1-yl)propyl)pentacosa-10,12-dienamide as a white solid (0.77 g, 80%).

N-(3-(1H-imidazol-1-yl)propyl)pentacosa-10,12-dienamide (0.70 g, 1.45 mmol) was added to 20 ml of acetonitrile containing bromoacetonitrile (0.28 g, 2.32 mmol), followed by refluxing while stirring overnight. Subsequently, a solid was obtained through concentration in vacuo. The solid was washed with hexane three times, thereby obtaining DA-1 (0.75 g, 86%) as a yellowish powder. m.p.: 89° C., IR (KBr, cm$^{-1}$): ν max 611, 624, 652, 719, 757, 860, 927, 1022, 1168, 1382, 1423, 1453, 1467, 1538, 1642, 1651, 2267, 2849, 2919, 3070, 3094, 3255, 3358. 1H NMR (600 MHz, dimethyl sulfoxide-d 6, δ): 9.39 (s, 1H), 7.96 (t, J=6 Hz, 1H), 7.95 (t, J=1.8 Hz, 1H), 7.93 (t, J=1.8 Hz, 1H), 5.63 (s, 2H), 4.22 (t, J=6.6 Hz, 2H), 3.05 (q, J=6 Hz, 2H), 2.26 (t, J=7.2 Hz, 4H), 2.06 (t, J=7.8 Hz, 2H), 1.92 (quint, J=6.6 Hz, 2H), 1.50-0.40 (m, 6H), 1.30-0.23 (m, 26H), 0.85 (t, J=7.2 Hz, 3H); 13 C NMR (75 MHz, CDCl3, δ): 174.82, 137.88, 123.53, 123.22, 114.08, 65.50, 65.44, 48.29, 38.71, 36.70, 35.77, 32.14, 29.88, 29.86, 29.72, 29.58, 29.34, 29.24, 29.11, 28.60, 26.04, 22.92, 19.44, 14.37.

Synthesis Example 2: Synthesis of DA-2 [3-(Cyanomethyl)-1-(3-(tricosa-10,12-dienamido)propyl)-1H-imidazol-3-ium bromide]

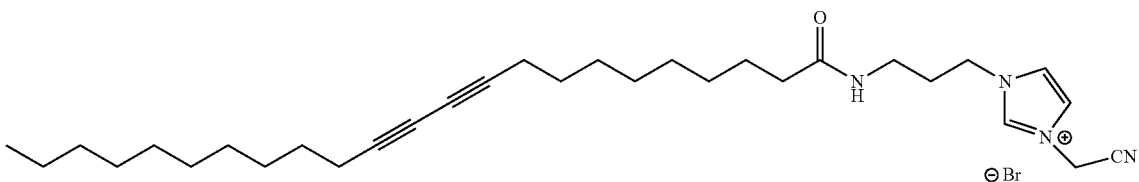

DA-2

2,5-dioxopyrrolidin-1-yltricosa-10,12-diynoate (TCDA-NHS, 0.89 g, 2.00 mmol) and TEA (0.41 g, 4 mmol) were dissolved in 10 ml of methylene chloride, thereby obtaining a first solution. 1-(3-aminopropyl)imidazole (0.38 g, 3.00 mmol) was dissolved in 10 ml of methylene chloride and then added to the first solution, followed by stirring at room temperature overnight. Subsequently, a residue was obtained through concentration in vacuo, and the residue was fed into a silica gel chromatography column (methylene chloride/methanol, 96/4), thereby obtaining N-(3-(1H-Imidazol-1-yl)propyl)tricosa-10,12-dienamide (0.74 g, 82%) as a white solid.

N-(3-(1H-Imidazol-1-yl)propyl)tricosa-10,12-dienamide (0.32 g, 0.70 mmol) was added to 20 ml of acetonitrile containing bromoacetonitrile (0.13 g, 1.06 mmol), followed by refluxing while stirring overnight. Subsequently, a solid was obtained through concentration in vacuo. The obtained solid was washed with hexane three times, thereby obtaining DA-2 (0.33 g, 83%) as a yellowish powder. IR (KBr, cm$^{-1}$): ν max 611, 624, 651, 721, 758, 859, 927, 1022, 1168, 1383, 1423, 1454, 1466, 1538, 1642, 1652, 2266, 2850, 2921, 3072, 3093, 3255, 3350. 1H NMR (600 MHz, dimethyl sulfoxide-d 6, δ): 9.38 (s, 1H), 7.95 (t, J=6 Hz, 1H), 7.94 (t, J=1.8 Hz, 1H), 7.92 (t, J=1.8 Hz, 1H), 5.62 (s, 2H), 4.22 (t, J=7.2 Hz, 2H), 3.05 (q, J=6.6 Hz, 2H), 2.26 (t, J=7.2 Hz, 4H), 2.06 (t, J=7.2 Hz, 2H), 1.92 (quint, J=6.6 Hz, 2H), 1.50-0.40 (m, 6H), 1.30-0.24 (m, 22H), 0.85 (t, J=7.2 Hz, 3H); 13 C NMR (75 MHz, dimethyl sulfoxide-d 6, δ): 173.12, 138.19, 123.87, 123.42, 115.42, 66.02, 47.87, 37.63, 36.08, 35.78, 31.99, 30.34, 29.58, 29.36, 29.09, 28.92, 28.87, 28.43, 28.39, 25.90, 22.79, 18.97, 14.65.

Synthesis Example 3: Synthesis of DA-3 [3-(Cyanomethyl)-1-(3-(heptadeca-4,6-dienamido) propyl)-1H-imidazol-3-ium bromide]

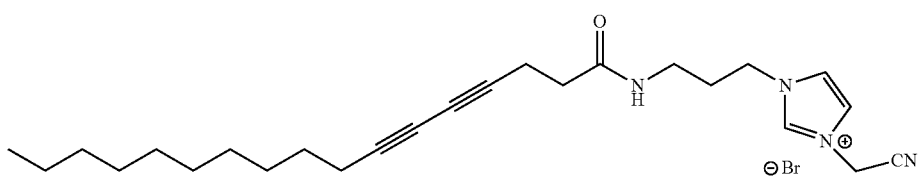

DA-3

2,5-dioxopyrrolidin-1-ylheptadeca-4,6-diynoate (HDDA-NHS, 0.72 g, 2.00 mmol) and TEA (0.41 g, 4 mmol) were dissolved in 10 ml of methylene chloride, thereby obtaining a first solution. 1-(3-aminopropyl)imidazole (0.38 g, 3.00 mmol) was dissolved in 10 ml of methylene chloride, thereby obtaining a second solution. The obtained second solution was added to the first solution, followed by stirring at room temperature overnight. Subsequently, a residue was obtained through concentration in vacuo. The obtained residue was fed into a silica gel chromatography column (methylene chloride/methanol, 96/4), thereby obtaining N-(3-(1H-Imidazol-1-yl)propyl)heptadeca-4,6-dienamide (0.57 g, 77%) as a yellow liquid.

N-(3-(1H-Imidazol-1-yl)propyl)heptadeca-4,6-dienamide (0.26 g, 0.70 mmol) was added to 20 ml of acetonitrile containing bromoacetonitrile (0.13 g, 1.06 mmol), followed by refluxing while stirring overnight. Subsequently, a solid was obtained through concentration in vacuo. The solid was washed with hexane three times, thereby obtaining DA-3 (0.29 g, 85%) as a yellowish powder. IR (KBr, cm$^{-1}$): ν max 610, 623, 720, 758, 859, 927, 1024, 1167, 1380, 1424, 1453, 1466, 1543, 1650, 2267, 2850, 2920, 3066, 3095, 3222, 3324. 1H NMR (600 MHz, CDCl3, δ): 10.09 (s, 1H), 8.04 (s, 1H), 7.78 (s, 1H), 7.76 (t, J=5.4 Hz, 1H), 6.04 (s, 2H), 4.46 (t, J=6 Hz, 2H), 3.27 (d, J=4.2 Hz, 2H), 2.59 (t, J=7.2 Hz, 2H), 2.50 (t, J=7.2 Hz, 2H), 2.23-0.16 (m, 4H), 1.48 (quint, J=7.8 Hz, 2H), 1.34-0.24 (m, 14H), 0.86 (t, J=6.6 Hz, 3H); 13 C NMR (75 MHz, CDCl3, δ): 172.20, 137.83, 123.33, 123.27, 114.09, 66.16, 65.23, 48.17, 38.71, 35.86, 34.77, 32.05, 29.84, 29.75, 29.68, 29.47, 29.28, 29.11, 28.54, 22.83, 19.38, 15.84, 14.28.

Synthesis Example 4: Synthesis of DA-4 [3-(Cyanomethyl)-1-(3-(pentacosa-10,12-dienamido) propyl)-1H-imidazol-3-ium chloride]

DA-4 was obtained in the same manner as in Synthesis Example 1, except that chloroacetonitrile was used instead of bromoacetonitrile. 1H NMR (600 MHz, CDCl3, δ): 10.32 (s, 1H), 7.92 (t, J=3 Hz, 1H), 7.79 (t, J=6 Hz, 1H), 7.74 (t, J=1.8 Hz, 1H), 6.01 (s, 2H), 4.40 (t, J=6.6 Hz, 2H), 3.22 (q, J=6 Hz, 2H), 2.24-2.20 (m, 6H), 2.12 (t, J=7.8 Hz, 2H), 1.57-1.46 (m, 6H), 1.34-1.23 (m, 26H), 0.85 (t, J=7.2 Hz, 3H).

Ink Preparation Example

DA-1 was dissolved in distilled water to obtain an aqueous DA-1 solution (100×10$^{-3}$ M). To lower the viscosity of the solution, the solution was diluted by adding ethanol (20 vol % with respect to distilled water), thereby preparing an ink.

Moisture Test Paper Manufacture Example

A black ink was removed from an inkjet cartridge (HP 703). The cartridge was washed with ethanol and water, followed by being dried while purging with nitrogen. The ink prepared according to the ink preparation example was put into the cartridge, and an arbitrary image was printed on A4 paper using an inkjet printer (HP Deskjet Ink Advantage K209g), followed by drying at room temperature for one or more minutes. An image was not observed immediately after the printing, but a blue image was exhibited by UV irradiation (254 nm, 1 mWcm$^{-2}$) for 30 seconds. Such a blue image may indicate that polydiacetylene is formed.

Moisture Test Paper Comparison Example 0.750 g of CsOH was dissolved in deionized water, and then 1.87 g of 10,12-pentacosadiynoic acid (PCDA) was dissolved in 9.6 mL of a tetrahydrofuran (THF) solvent. Subsequently, the CsOH solution was added to the PCDA solution dropwise, followed by mixing. A composite solution obtained by stirring for one hour to be uniformly mixed was put into a cartridge and was printed on A4 paper using an inkjet printer (HP Deskjet Ink Advantage K209g), followed by drying at room temperature for one or more minutes. An image was not observed immediately after the printing, but a blue image was exhibited by UV irradiation (254 nm, 1 mWcm$^{-2}$) for 30 seconds. Such a blue image may indicate that polydiacetylene is formed.

FIG. 4 is a set of schematic diagrams illustrating a moisture test paper manufactured according to the moisture test paper manufacture example and results obtained by applying moisture to a selected region of the moisture test paper.

Referring to FIG. 4, an original image was printed on A4 paper using the ink prepared according to the ink preparation example, but the printed image (DA-1 printing) was colorless and transparent, thus not being observed with the naked eye. Subsequently, a blue image (UV irradiation) having different grayscales was exhibited by UV irradiation (254

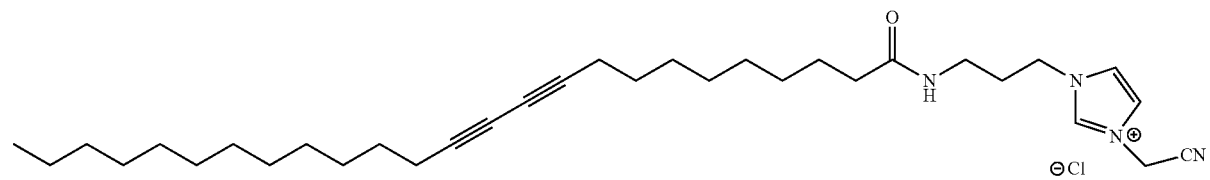

DA-4 nm, 1 mWcm$^{-2}$) for 30 seconds. Such a blue image indicates that polydiacetylene was formed, and different grayscales of the image may indicate that the concentration of polydiacetylene in the printed region is varied. Subsequently, water was printed on regions corresponding to red regions of an original image at room temperature. As a result, the color of the corresponding regions was changed to red to produce red images (water-jet printing image), and regions on which water had not been printed maintained original blue images. The red images may indicate that the main chains of polydiacetylene have been distorted. The grayscales of the red images may also indicate that the amount of water applied is varied.

FIGS. 5A-5D illustrate graphs of a) UV-vis absorption spectrum, b) fluorescence emission spectrum, and c, d) Raman spectrum before and after applying moisture to the moisture test paper manufactured according to the moisture test paper manufacture example.

Referring to FIG. 5A it can be confirmed that a maximum absorption wavelength of about 640 nm (blue) before exposure to moisture shifts to a maximum absorption wavelength of about 540 nm (red) after exposure to moisture. This result indicates that main chains of polydiacetylene have been distorted.

Referring to FIG. 5B it can be confirmed that, when the test paper is irradiated with 488 nm excitation light, fluorescence is not generated before exposure to moisture, but a fluorescence emission band is exhibited at 550 nm after exposure to moisture.

Referring to FIG. 5C it can be confirmed that, when bands before exposure to moisture are compared to those after exposure to moisture, 2079 and 1452 cm$^{-1}$ bands corresponding to alkyne-alkene bands are respectively shifted to 2120 and 1515 cm$^{-1}$ bands.

Referring to FIG. 5D when examining a C—C stretching region associated with an aliphatic alkyl chain structure, a strong Raman band is observed at 1081 cm$^{-1}$ and weak two bands are exhibited at 1105 and 1126 cm$^{-1}$ before exposure to moisture. These correspond to alkyl chains having an all-trans form. However, it can be confirmed that all of the three bands disappeared and one main band is observed at 1068 cm$^{-1}$ after exposure to moisture. From this data, it can be confirmed that the all-trans C—C form before exposure to moisture is changed into a gauche form.

From the results of FIGS. 5C and 5D, it can be assumed that not only the form of the aliphatic alkyl chains is changed but also distortion of main chains occurs after exposure to moisture. Accordingly, it was assumed that effective pi-orbital superposition was interrupted and thus the transition from blue to red occurred.

FIGS. 6A-6C are a set of photographs illustrating the temperature-dependent reaction of the moisture test paper manufactured according to the moisture test paper manufacture example and solubility of DA-1 in water dependent upon temperature.

Referring to FIG. 6A the color of a blue polydiacetylene region was not changed when rubbed with ice, but, when a region in contact with ice was contacted with a finger of an experimenter, the color of the region was clearly changed to red.

Referring to FIG. 6B when a circle was drawn using 0° C. cold water on a blue polydiacetylene region and then temperature was elevated, a red circle was observed at about 20° C. and the color of the red circle became clearer as temperature was elevated to 25° C. and 30° C.

Referring to FIG. 6C when a sample including DA-1 and water was put into a plastic bag, the plastic bag was put on a paper on which "A" was printed, and temperature was elevated, the lower "A" began to be observed from about 20° C. and became clearer as temperature was elevated to 25° C. and 30° C.

Referring to FIGS. 6A-6C again, it can be assumed that distortion of main chains of polydiacetylene occurs when non-polymerized diacetylene remaining in the polydiacetylene region is dissolved in water, which induces color change from blue to red.

FIG. 7 is a photograph illustrating a relative humidity-dependent hydrochromic degree of the moisture test paper manufactured according to the moisture test paper manufacture example. In particular, a hydrochromic degree when exposed for 30 minutes at a specific relative humidity is illustrated.

Referring to FIG. 7, the moisture test paper manufactured according to the moisture test paper manufacture example did not change color when exposed to a relative humidity of 20 to 95% for 30 minutes. However, the color of the moisture test paper was changed to red when exposed to a relative humidity of 100%. From these results, it can be confirmed that the moisture test paper according to the example is not greatly affected by the humidity of the surrounding environment, and changes color only when directly exposed to water.

FIG. 8 is a set of photographs illustrating hydrochromic characteristics of the moisture test papers according to the moisture test paper manufacture example (b) and the moisture test paper comparison example (a).

Referring to FIG. 8, it can be confirmed that the test paper according to the moisture test paper comparison example (a) does not change color by water, but the color of the test paper according to the moisture test paper manufacture example (b) is changed to red by water. From these results, it can be confirmed that polydiacetylene formed from the diacetylene monomer according to the examples of the present invention, particularly the diacetylene monomer having a quaternary ammonium ion at an end thereof represented by Formula 1, exhibits hydrochromic characteristics.

Sweat Pore Mapping Example

The fingertip, the palm, and/or the sole were/was gently brought into contact with the moisture test paper according to the moisture test paper manufacture example.

FIG. 9 illustrates an optical image and a fluorescence image after a thumb touches the moisture test paper manufactured according to the moisture test paper manufacture example. Fluorescent microdots representing sweat-secretory active pores were analyzed using a fluorescence spectrometer (510 to 550 nm excitation)

Referring to FIG. 9, red dots, which are produced due to a very small amount of sweat secreted from sweat pores and correspond to the sweat pores, are generated on a blue polydiacetylene paper film shown in an optical image on the left. Using this, the distribution of sweat pores may be analyzed.

In addition, the distribution of sweat pores may be analyzed by obtaining red fluorescence images expressed by sweat secreted at the positions of sweat pores from the fluorescence image on the right.

FIG. 10 illustrates fluorescence images obtained after respectively contacting a thumb on four different moisture test papers manufactured according to the moisture test paper manufacture example.

Referring to FIG. 10, when the four sweat pore distribution maps were superimposed, positions thereof overlap, which indicates that sweat pore distribution analysis using the hydrochromic polydiacetylene is reliable.

FIG. 11 illustrates comparison photographs of a fluorescence image obtained after a thumb contacts the moisture test paper manufactured according to the moisture test paper manufacture example and a potential fingerprint obtained using the same thumb and ninhydrin.

Referring to FIG. 11, when the two images were superimposed, the sweat pores observed from the moisture test paper and the potential fingerprint through ninhydrin perfectly matched.

FIG. 12 illustrates a threshold image (a-2) in which only sweat pores are exposed, using a position tracking method, from a sweat pore distribution (a-1) obtained using the moisture test paper manufactured according to the moisture test paper manufacture example, a sweat pore distribution (b-1) for the same finger obtained using ninhydrin, and a threshold (b-2) image in which only sweat pores are exposed, using position tracking, from the sweat pore distribution (b-1).

Referring to FIG. 12, it can be confirmed that the positions of the sweat pores match well from a-3 and b-3 images when coincidence of the two sweat pore distributions was comparatively analyzed using a computer program.

FIG. 13 illustrates sweat pore distribution test results on the entire palm of a hand using a moisture test paper.

Referring to FIG. 13, a is a photograph of a palm-shaped image on a moisture test paper obtained according to the moisture test paper manufacture example, and b illustrates sweat pore distribution (fluorescence) of the entire palm obtained by lightly pressing the palm on the manufactured moisture test paper. All red dots shown in b indicate a color change in hydrochromic polydiacetylene and fluorescence expression positions due to sweat secreted from sweat pores of the palm, which may be used to analyze the distribution of sweat pores. b-1 illustrates an enlargement of a palm area under a thumb and indicates that a sweat pore distribution may be effectively obtained.

FIG. 14 illustrates test results of the distribution of sweat pores in the sole using a moisture test paper.

Referring to FIG. 14, a is a photograph of the sole, and b illustrates an entire sweat pore distribution (optical) of the sole obtained by pressing the sole on the moisture test paper obtained according to the moisture test paper manufacture example. It can be confirmed that red dots are present along the sole shape on the hydrochromic polydiacetylene paper film with a blue background. The red dots correspond to positions at which a color change in the hydrochromic polydiacetylene and fluorescence expression occurred due to sweat secreted from sweat pores of the sole. c illustrates an enlargement of the heel of the sole and indicates that a sweat pore distribution may be effectively obtained.

FIG. 15 illustrates test results of the distribution of sweat pores in the back using a moisture test paper.

Referring to FIG. 15, the positions, at which a color change in hydrochromic polydiacetylene and fluorescence expression occur, of sweat pores in the back may be observed.

Referring to FIGS. 13, 14, and 15 again, all body parts having sweat pores from which sweat is secreted may be subjected to sweat pore distribution analysis using the hydrochromic polydiacetylene paper film, i.e., the moisture test paper, although there are differences according to the amount of sweat secreted.

FIG. 16 is a set of photographs illustrating thumb sweat pore distribution test results of moisture test films manufactured by subjecting an A4 paper, a Kent paper, an OHP film, and a PET film, which have been printed with the ink prepared according to the ink preparation example, to UV irradiation (254 nm, 1 mWcm$^{-2}$) for 30 seconds. In particular, the thumb bottom was touched on each of the substrates for about 1 second, and then the substrates were observed through a fluorescence microscope.

Referring to FIG. 16, it can be confirmed that the ink prepared according to the ink preparation example may be used to manufacture moisture test films exhibiting hydrochromic characteristics due to a small amount of moisture secreted from sweat pores using any substrate.

Although the present invention has been described in detail with reference to the preferred embodiments, those skilled in the art will appreciate that the scope of the present invention is not limited to the embodiments and various modifications and changes are possible within the technical spirit and scope of the present invention.

The invention claimed is:

1. A water-based ink, comprising:
   a diacetylene monomer represented by Formula 1 below; and
   a solvent mixture comprising water and an alcohol,

[Formula 1]

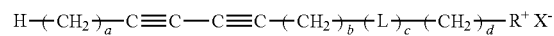

wherein a is an integer of 1 to 20, b is an integer of 1 to 20, c is an integer of 0 to 2, d is an integer of 1 to 10, L is

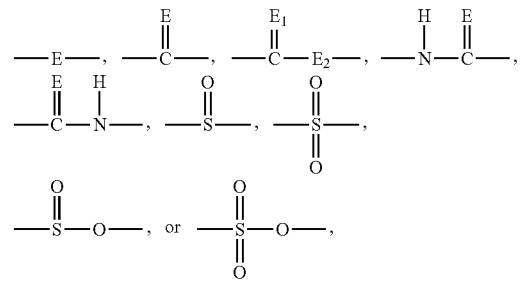

E, $E_1$, and $E_2$ are each independently O or S, $X^-$ is $F^-$, $Cl^-$, $Br^-$, $I^-$, $PF_6^-$, $BF_4^-$, bis(trifluoromethane)sulfonimide ($Tf_2N^-$), trifluoromethanesulfonate ($TfO^-$), $SCN^-$, or $CH_3COO^-$, and $R^+$ is $N^+$—$R^+$-heterocyclic quaternary ammonium represented by Formula 2a below:

[Formula 2a]

wherein ring B is a 5-membered or 6-membered heterocyclic compound having 1 to 3 atoms of N and 0 to 1 atoms of O as heteromembers, $R_1$ is a C1 to C16 cyanoalkyl, a C1 to C16 haloalkyl, a C1 to C16 hydroxyalkyl, or a C1 to C16 aminoalkyl, and * represents a bond.

2. The water-based ink according to claim 1, wherein the $N^+$—$R_1$-heterocyclic quaternary ammonium represented by Formula 2a is $N^+$—$R_1$-heterocyclic quaternary ammonium represented by Formula 2b or 2c below:

[Formula 2b]

[Formula 2c]

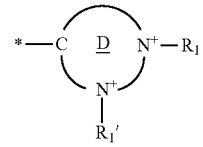

wherein, in Formula 2b, ring C is a 5-membered or 6-membered unsaturated heterocyclic compound comprising 2 to 3 atoms of N as heteromembers, in Formula 2c, ring D is a 5-membered or 6-membered unsaturated heterocyclic compound comprising 2 to 3 atoms of N as heteromembers, and R1 and R1' are each independently a C1 to C16 cyanoalkyl, a C1 to C16 haloalkyl, a C1 to C16 hydroxyalkyl, or a C1 to C16 aminoalkyl.

3. The water-based ink according to claim 1, wherein the $N^+$—$R_1$-heterocyclic quaternary ammonium is $N^+$—$R_1$-azolium, $N^+$—$R_1$-azinium, or $N^+$—$R_1R_2$-piperazinium.

4. The water-based ink according to claim 3, wherein the $N^+$—$R_1$-azolium is $N^+$—$R_1$-diazolium or $N^+$—$R_1$-triazolium.

5. The water-based ink according to claim 4, wherein the $N^+$—$R_1$-diazolium is $N^+$—$R_1$-imidazolium represented by Formula 2-1 below or $N^+$—$R_1$-pyrazolium represented by Formula 2-2 below:

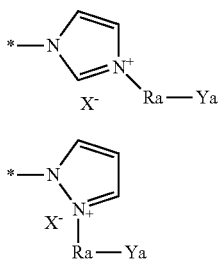

(2-1)

(2-2)

wherein $R_a$ is a C1 to C16 alkylene group, and $Y_a$ is a cyano group, a halogen, a hydroxyl group, or an amine group.

6. The water-based ink according to claim 4, wherein the $N^+$—$R_1$-triazolium is represented by Formula 2-3 below:

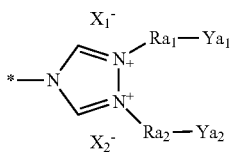

(2-3)

wherein $R_{a1}$ and $R_{a2}$ are each independently a C1 to C16 alkylene group, $Y_{a1}$ and $Y_{a2}$ are each independently a cyano group, a halogen, a hydroxyl group, or an amine group, $X_1^-$ is the same as $X^-$ in Formula 1, and $X_2^-$ is the same as $X^-$ in Formula 1.

7. The water-based ink according to claim 1, wherein a volumetric ratio of the water to the alcohol is 1:0.03 to 1:0.7.

8. The water-based ink according to claim 1, wherein the diacetylene monomer is contained at a concentration of 50 to 300 mM.

9. A moisture test paper, comprising:

a paper substrate comprising cellulose fibers which are irregularly entangled; and a polydiacetylene region comprising hydrochromic polydiacetylene represented by Formula 3 below disposed on the paper substrate:

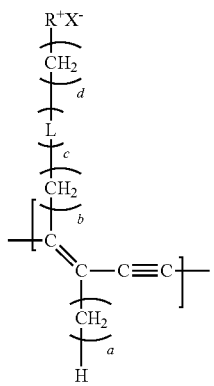

[Formula 3]

wherein a is an integer of 1 to 20, b is an integer of 1 to 20, c is an integer of 0 to 2, d is an integer of 1 to 10, L is

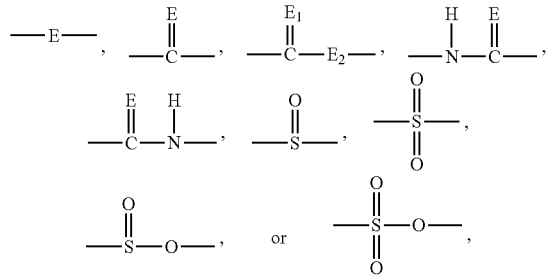

E, $E_1$, and $E_2$ are each independently O or S, $X^-$ is $F^-$, $Cl^-$, $Br^-$, $I^-$, $PF_6^-$, $BF_4^-$, bis(trifluoromethane)sulfonimide ($Tf_2N^-$), trifluoromethanesulfonate ($TfO^-$), $SCN^-$, or $CH_3COO^-$, and $R^+$ is $N^+$—$R_1$-heterocyclic quaternary ammonium represented by Formula 2a below:

[Formula 2a]

wherein ring B is a 5-membered or 6-membered heterocyclic compound having 1 to 3 atoms of N and 0 to 1 atoms of O as heteromembers, $R_1$ is a C1 to C16 cyanoalkyl, a C1 to C16 haloalkyl, a C1 to C16 hydroxyalkyl, or a C1 to C16 aminoalkyl, and * represents a bond.

10. The moisture test paper according to claim 9, wherein the polydiacetylene region is blue.

11. The moisture test paper according to claim 9, wherein the polydiacetylene region changes color by water at 20° C. or more.

12. The moisture test paper according to claim 9, wherein —OH groups of the cellulose fibers of the paper substrate are exposed.

13. The moisture test paper according to claim 9, wherein the moisture test paper is a paper for mapping sweat pores.

14. A method of manufacturing a moisture test paper, the method comprising:

a step of printing the water-based ink containing diacetylene monomers according to claim 1 on a paper substrate comprising cellulose fibers which are irregularly entangled;

a step of drying the ink printed on the paper substrate to form a diacetylene region in which the diacetylene monomers are self-assembled and disposed; and a step of irradiating the diacetylene region with ultraviolet rays or gamma rays to photopolymerize the diacetylene monomers and, accordingly, form hydrochromic polydiacetylene.

15. The method according to claim 14, wherein —OH groups of the cellulose fibers of the paper substrate are exposed.

16. The method according to claim 14, wherein the moisture test paper is a paper for mapping sweat pores.

* * * * *